United States Patent

Venet et al.

Patent Number: 5,589,484
Date of Patent: Dec. 31, 1996

[54] 4-QUINOLINYL DERIVATIVES

[75] Inventors: Marc G. Venet, Le Mesnil Esnard; Jérôme E. G. Guillemont, Oissel; Daniel F. J. Vernier, Rouen, all of France; Frank C. Odds, Schilde, Belgium

[73] Assignee: Janssen Pharmaceutica N.V., Beerse, Belgium

[21] Appl. No.: 428,176

[22] PCT Filed: Oct. 19, 1993

[86] PCT No.: PCT/EP93/02884

§ 371 Date: Apr. 4, 1995

§ 102(e) Date: Apr. 4, 1995

[87] PCT Pub. No.: WO94/10164

PCT Pub. Date: May 11, 1994

[51] Int. Cl.$^6$ .......................... C07D 403/06; A61K 31/47
[52] U.S. Cl. ............................ 514/314; 546/176
[58] Field of Search ............................ 546/176; 514/314

[56] References Cited

U.S. PATENT DOCUMENTS

| | | | |
|---|---|---|---|
| 5,028,606 | 7/1991 | Venet | 514/249 |
| 5,037,829 | 8/1991 | Freyne | 514/259 |
| 5,185,346 | 2/1993 | Sanz | 514/312 |

FOREIGN PATENT DOCUMENTS 371564  11/1989  European Pat. Off.

*Primary Examiner*—David B. Springer
*Attorney, Agent, or Firm*—Charles J. Metz

[57] ABSTRACT

The present invention is concerned with novel quinoline derivatives having anti-Helicobacter activity of formula

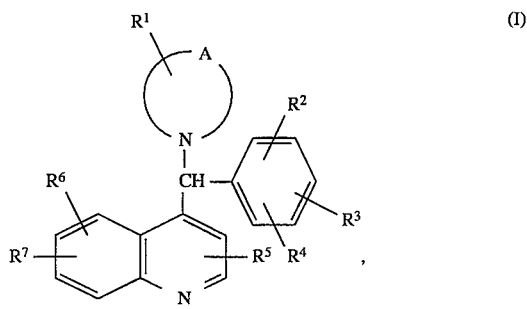

(I)

the pharmaceutically acceptable acid addition salts thereof, the stereochemically isomeric forms thereof, the quaternized forms thereof and the N-oxides thereof, wherein —A— represents a bivalent radical of formula

| | |
|---|---|
| —N=CH—CH=CH— | (a), |
| —CH=N—CH=CH— | (b), |
| —N=N—CH=CH— | (c), |
| —N=CH—N=CH— | (d), |
| —N=CH—CH=N— | (e), |
| —CH=N—N=CH— | (f), |
| —N=N—N=CH— | (g), |
| —N=N—CH=N— | (h), | or

| | |
|---|---|
| —CH=CH—CH=CH— | (i); |

$R^1$, $R^2$, $R^3$, $R^4$, $R^5$, $R^6$ and $R^7$ each independently represent hydrogen, halo, hydroxy, $C_{1-4}$alkyloxy, $C_{1-4}$alkyl, trifluoromethyl, amino, mono- or di($C_{1-4}$alkyl)amino or nitro, provided that when one substituent on a phenyl group is a nitro then the other substituents on said phenyl group are other than nitro; novel compositions comprising said compounds, processes of preparing said compounds and compositions and methods for treating subjects suffering from disorders or afflictions associated with Helicobacter infection.

15 Claims, No Drawings

4-QUINOLINYL DERIVATIVES

CROSS-REFERENCE TO RELATED APPLICATIONS

This application is based upon PCT application Ser. No. PCT/EP 93/02884, filed Oct. 19, 1993, which claims priority from U.S. application Ser. Nos. 07/967,008, filed on Oct. 27, 1992, and 08/069,804, filed Jun. 1, 1993, both of which are now abandoned.

BACKGROUND OF THE INVENTION

EP-0,371,564 (published Jun. 6, 1990) discloses (1 H-azol-1-yl-methyl) substituted quinoline derivatives which suppress the plasma elimination of retinoic acids. The compounds of the present invention differ from the cited art compounds by the fact that the quinoline moiety is substituted at the 4-position with a (phenyl azolyl)methyl group and by their unexpected anti-Helicobacter activity.

Afflictions of the gastro-enteric tract are widespread. Modern medicine still fails to cure a lot of them, in particular those related to the presence in the gastric mucosa of the bacterium Helicobacter, e.g. chronic gastritis, duodenal ulcer and duodenal ulcer relapse. Dual therapies in the eradication of Helicobacter, comprising the separate administration of two antibiotic drugs, have not been satisfactory up till now, because of one or more of the following reasons: a low eradication rate, numerous side effects and development of resistance by Helicobacter.

Triple therapies comprising the administration of two antibiotics and a bismuth compound have been shown to be effective, but are very demanding for the patients and are also complicated by side effects.

The present invention is concerned with novel quinoline compounds which are potent anti-Helicobacter agents and which may be used in a mono therapy in the eradication of *Helicobacter pylori* and related species.

DESCRIPTION OF THE INVENTION

The present invention is concerned with novel quinoline derivatives of formula

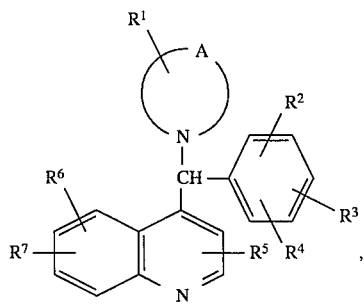

(I)

the pharmaceutically acceptable acid addition salts thereof, the stereochemically isomeric forms thereof, the quaternized forms thereof and the N-oxides thereof, wherein —A— represents a bivalent radical of formula —N=CH—CH=CH— (a),
—CH=N—CH=CH— (b),
—N=N—CH=CH— (c),
—N=CH—N=CH— (d),
—N=CH—CH=N— (e),
—CH=N—N=CH— (f),
—N=N—N=CH— (g),
—N=N—CH=N— (h), or —CH=CH—CH=CH— (i);

$R^1$, $R^2$, $R^3$, $R^4$, $R^5$, $R^6$ and $R^7$ each independently represent hydrogen, halo, hydroxy, $C_{1-4}$alkyloxy, $C_{1-4}$alkyl, trifluoromethyl, amino, mono- or di-($C_{1-4}$alkyl)amino or nitro, provided that when one substituent on a phenyl group is a nitro then the other substituents on said phenyl group are other than nitro.

As used in the foregoing definitions and hereinafter halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl.

The term pharmaceutically acceptable acid addition salt as used hereinbefore defines the non-toxic, therapeutically active acid addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are inorganic acids such as hydrohalic acid, i.e. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term pharmaceutically acceptable acid addition salts also comprises the solvates which the compounds of formula (I) may form, e.g. the hydrates, alcoholates and the like.

The term stereochemically isomeric forms refers to those compounds with identical molecular formulae but differing in the arrangement of their atoms in space. Unless otherwise mentioned or indicated, the chemical designation of compounds denotes the mixture of all possible stereochemically isomeric forms, said mixtures containing equal proportions of all diastereomers and enantiomers of the basic molecular structure. Mixtures containing equal amounts of enantiomers are called 'racemic mixtures'. Enantiomerically pure forms or mixtures containing unequal proportions of enantiomers may be characterized by their optical activity. An optically active substance is described as dextrorotatory or levorotatory and specified as the (+)- or (−)-isomer, respectively. All stereochemically isomeric forms of the compounds of formula (I) both in pure form or in admixture with each other are intended to be embraced within the scope of the present invention.

From formula (I) it is evident that the compounds of this invention have at least one asymmetric carbon atom in their structure, namely the carbon atom bearing the quinoline, phenyl and azole substituent. The absolute configuration of this center may be indicated by the stereochemical descriptors R and S.

Some compounds of the present invention may exist in different tautomeric forms and all such tautomeric forms are intended to be included within the scope of the present invention.

As defined hereinabove, the invention also comprises the quaternized forms of the compounds of formula (I), said quaternized forms being represented by the formula

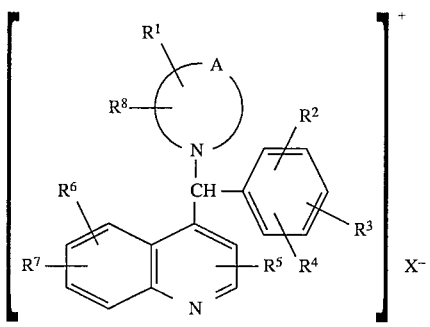

(I-a)

wherein A, $R^1$, $R^2$, $R^3$, $R^4$, $R^5$, $R^6$ and $R^7$ are as defined hereinabove and $R^8$ represents $C_{1-4}$alkyl which is linked to a nitrogen atom of the bivalent radical —A—. In this way, the positive charge will be located on the nitrogen atom bearing the $R^8$ substituent. $X^-$ is an organic or inorganic anion and preferably is hydroxide, alkyloxide or an anion arising from an acid such as hydrofluoric acid, hydrochloric acid, hydrobromic acid, hydroiodic acid, sulfuric acid, nitric acid, chloric acid, perchloric acid, phosphoric acid, 4-methylbenzenesulfonic acid, benzenesulfonic acid, methanesulfonic acid, trifluoromethylsulfonic acid, acetic acid, benzoic acid, chloroacetic acid, phthalic acid, maleic acid, malonic acid, citric acid and the like.

Further, the invention relates also to the N-oxides of the compounds of formula (I). These N-oxides refer to those compounds of formula (I) that are oxidized to tertiary amine oxides, wherein the nitrogen and the oxygen bear (+) and (−) formal charges, respectively. Preferably the nitrogen atom forming part of the quinoline ring system may be oxidized.

$R^1$ is suitably hydrogen; $C_{1-4}$alkyl, especially ethyl or methyl; hydroxy; $C_{1-4}$alkyloxy, especially ethoxy or methoxy; nitro; amino; mono- or di($C_{1-4}$alkyl)amino.

$R^2$ is suitably hydrogen; halo, especially bromo, chloro or fluoro; trifluoromethyl; hydroxy; or $C_{1-4}$alkyloxy, especially methoxy.

$R^3$ and $R^4$ are suitably hydrogen; halo; trifluoromethyl; hydroxy; or $C_{1-4}$alkyloxy.

$R^5$ is suitably hydrogen; halo; hydroxy; $C_{1-4}$alkyl, especially methyl; or $C_{1-4}$alkyloxy.

$R^6$ and $R^7$ each independently suitably are hydrogen; halo, especially fluoro, chloro, bromo; hydroxy; $C_{1-4}$alkyloxy, especially methoxy; or trifluoromethyl.

Interesting compounds are those compounds of formula (I) wherein —A— represents a bivalent radical of formula —N=CH—CH=CH— (a)

or

—CH=N—CH=CH— (b).

Further interesting compounds are those compounds of formula (I) wherein —A— represents a bivalent radical of formula —N=N—CH=CH— (c), —N=CH—N=CH— (d), —N=CH—CH=N— (e), or —CH=N—N=CH— (f).

Another group of interesting compounds are those compounds of formula (I) wherein —A— represents a bivalent radical of formula —N=N—N=CH— (g), or —N=N—CH=N— (h).

A further group of interesting compounds are those compounds of formula (I), wherein —A— represents a bivalent radical of formula —CH=CH—CH=CH— (i).

Yet another group of interesting compounds are those compounds of formula (I) wherein $R^5$, $R^6$ and $R^7$ represent hydrogen.

Particular compounds are those compounds of formula (I) wherein $R^1$ is hydrogen.

Another group of particular compounds are those compounds of formula (I) wherein $R^2$ and $R^3$ are hydrogen and $R^4$ is halo, especially chloro or fluoro, preferably $R^4$ is substituted on the 3-position of the phenylmoiety.

Yet another group of particular compounds are those compounds of formula (I), wherein $R^5$ and $R^6$ each independently are hydrogen or halo and $R^7$ is hydrogen or halo, especially chloro or fluoro, preferably $R^7$ is substituted on the 5- or 8-position of the quinolinyl moiety.

Preferred compounds are those compounds of formula (I) wherein $R^1$ represents hydrogen, $C_{1-4}$alkyl, hydroxy, $C_{1-4}$alkyloxy, nitro, amino or mono- or di($C_{1-4}$alkyl)amino;

$R^2$, $R^3$ and $R^4$ each independently represent hydrogen, halo, trifluoromethyl, hydroxy or $C_{1-4}$alkyloxy;

$R^5$ represents hydrogen, halo, hydroxy or $C_{1-4}$alkyloxy;

$R^6$ and $R^7$ each independently represent hydrogen, halo, hydroxy, $C_{1-4}$alkyloxy or trifluoromethyl.

More preferred compounds are those preferred compounds wherein $R^1$, $R^2$, $R^3$, $R^5$ and $R^6$ represent hydrogen, and $R^4$ and $R^7$ each independently represent hydrogen or halo.

Still more preferred compounds are those more preferred compounds wherein —A— represents a bivalent radical of formula —N=N—CH=CH— (c)

or

—N=CH—N=CH— (d)

and $R^4$ is 3-halo.

The most preferred compound is 4-[(3-chlorophenyl)(1H-1,2,4-triazol-1-yl)methyl]quinoline, a pharmaceutically acceptable acid addition salt thereof, a stereochemically isomeric form thereof, a quaternized form thereof or an N-oxide thereof.

The compounds of formula (I) can be prepared by N-alkylating an azole of formula (II) with an intermediate of formula (III).

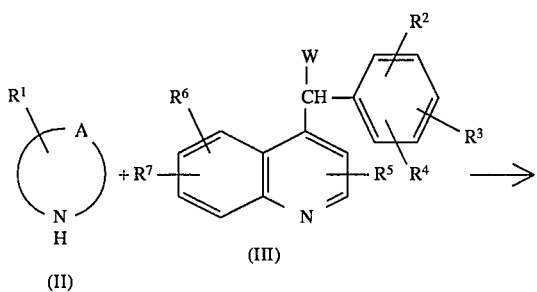

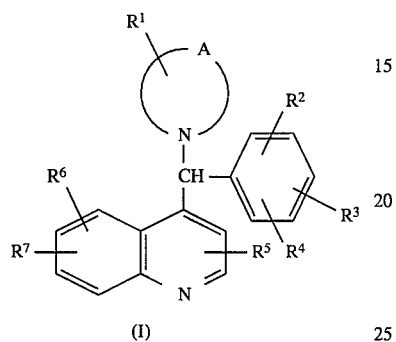

In formula (III) and hereinafter W represents an appropriate leaving group such as, for example, halo, e.g. chloro, bromo, iodo and the like; or a sulfonyloxy group such as, for example, methanesulfonyloxy, 4-methylbenzenesulfonyloxy and the like.

Said N-alkylation reaction can conveniently be conducted in a reaction-inert solvent such as, for example, an aromatic hydrocarbon, e.g. benzene, methylbenzene, dimethylbenzene and the like; an alkanol, e.g. methanol, ethanol, 1-butanol and the like; a ketone, e.g. 2-propanone, 4-methyl-2-pentanone and the like; an ether, e.g. tetrahydrofuran, 1,4-dioxane, 1,1'-oxybisethane, 1,1'-oxybis(2-methoxyethane) and the like; a dipolar aprotic solvent, e.g. N,N-dimethylformamide, N,N-dimethylacetamide, dimethyl sulfoxide, nitrobenzene, 1-methyl-2-pyrrolidinone, acetonitrile and the like; a halogenated hydrocarbon, e.g. dichloromethane, 1,2-dichloroethane and the like; or a mixture of such solvents. The addition of an appropriate base such as, for example, an alkali or an earth alkaline metal carbonate, hydrogen carbonate, alkoxide, hydride, amide, hydroxide or oxide, e.g. sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g. N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. In some instances it may be advantageous to use an excess of the azole (II) or to convert the azole first into a suitable salt form thereof such as, for example, an alkali or earth alkaline metal salt, by reacting (II) with an appropriate base as defined hereinabove and subsequently using said salt form in the reaction with the alkylating reagent of formula (III). Additionally, it may be advantageous to conduct said N-alkylation reaction under an inert atmosphere such as, for example, oxygen-free argon or nitrogen gas. Alternatively, said N-alkylation may be carried out by applying an-known conditions of phase transfer catalysis reactions.

In this and the following preparations, the reaction products may be isolated from the medium and, if necessary, further purified according to methodologies generally known in the art such as, for example, extraction, crystallization and chromatography.

Alternatively, the compounds of formula (I) may be prepared by N-alkylating an azole of formula (II) with an intermediate of formula (IV) in a reaction-inert solvent as defined hereinbefore and preferably in the presence of a reagent transforming the hydroxy in intermediate (IV) in a better leaving group, e.g. triphenylphosphine and diethyl azodicarboxylate.

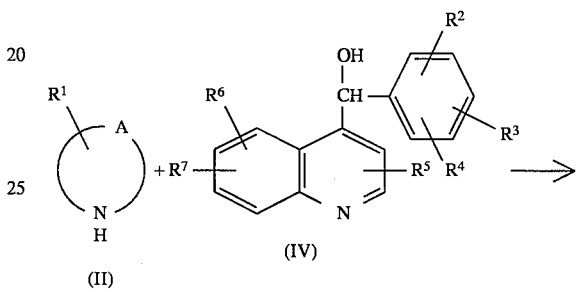

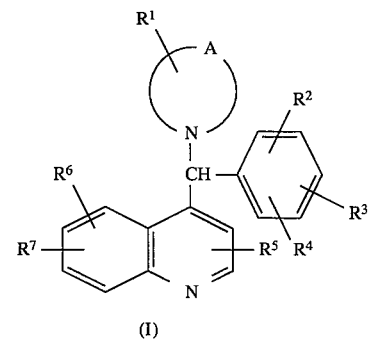

Further, the compounds of formula (I) wherein —A— is a radical of formula (i), said compounds being represented by the formula (I-b), may be prepared by reacting an intermediate of formula (V) with a reagent of formula (VI) wherein $W^1$ is a reactive leaving group, e.g. $C_{1-4}$alkyloxy, optionally in the presence of an acid, e.g. acetic acid.

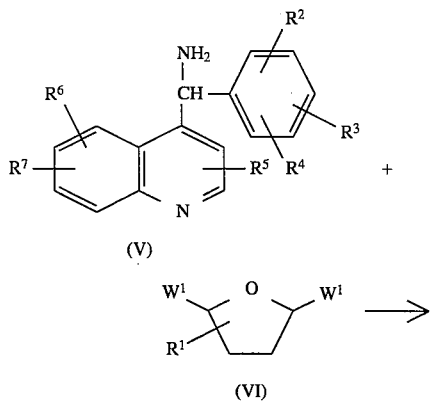

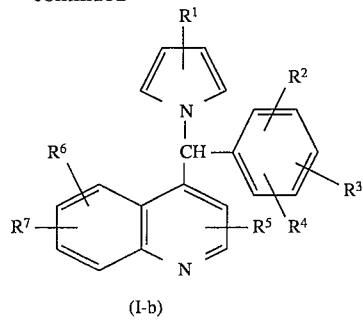

(I-b)

The compounds of formula (I) wherein —A— is a radical of formula (f) and $R^1$ is hydroxy, said compounds being represented by the formula (I-c), can be prepared by reacting an intermediate of formula (VII) with methanimidamide or a derivative thereof in a reaction-inert solvent, e.g. ethanol.

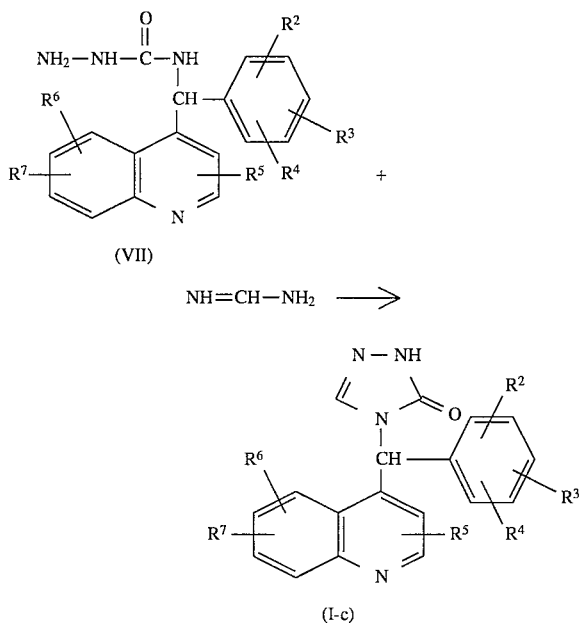

The quaternized forms of the compounds of formula (I-a) can conveniently be prepared by reacting a compound of formula (I) with a reagent of formula $R^8$-W (VIII), wherein $R^8$ and W are as defined hereinabove; thus preparing those quaternary compounds of formula (I-a) as defined hereinabove, wherein X is W. The reaction of (I) with (VIII) is preferably conducted in a suitable solvent such as, for example, a hydrocarbon, e.g. hexane, heptane, benzene, methylbenzene, dimethylbenzene and the like; an alcohol, e.g. methanol, ethanol, 2-propanol, 1-butanol and the like; an ether, e.g. 1,1'-oxybisethane, tetrahydrofuran, 1,4-dioxane and the like; a ketone, e.g. 2-propanone, 2-butanone and the like, a halogenated hydrocarbon, e.g. tetrachloromethane, trichloromethane, dichloromethane and the like; a dipolar aprotic solvent; e.g. N,N-dimethylformamide, N,N-dimethylacetamide, dimethyl sulfoxide, acetonitrile and the like. In some instances, it may be appropriate to conduct the reaction at elevated temperatures. If desired, the anion W in the products obtained according to the above procedures can be exchanged for another anion thus obtaining other quaternary salts of formula (I-a). Such anion-exchange reaction can conveniently be perforated following art-known procedures, e.g. by using an anionic exchange column, or by converting the quaternary salt into the corresponding hydroxide with a basic anion exchanger and subsequently reacting said hydroxide with the appropriate acid.

The N-oxides of the compounds of formula (I) can conveniently be prepared by N-oxidizing a compound of formula (I). Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t. butyl hydroperoxide and the like. If desired, said N-oxidation may be carried out in a suitable solvent such as, for example, water, a lower alkanol, e.g. methanol, ethanol, propanol, butanol and the like, a hydrocarbon, e.g. benzene, methylbenzene, dimethylbenzene and the like, a ketone, e.g. 2-propanone, 2-butanone and the like, and mixtures of such solvents. In order to enhance the reaction rate, it may be appropriate to heat the reaction mixture.

Enantiomerically pure forms of the compounds of formula (I) can be obtained by converting the racemic mixture of a compound of formula (I) with a suitable resolving reagent such as, for example, a chiral acid, e.g. tartaric, malic and mandelic acids, to a mixture of diastereomeric salts; physically separating said mixture by, for example, selective crystallization and the like methods; and finally converting said separated diastereomeric salts into the corresponding enantiomeric forms of the compound of formula (I) by hydrolysis in a basic aqueous medium, optionally at an elevated temperature.

Alternatively, enantiomerically pure forms can conveniently be obtained from the enantiomerically pure isomeric forms of the appropriate starting materials, provided that the subsequent reactions occur stereospecifically.

As a further alternative, the enantiomers may be separated by liquid chromatography using a chiral stationary phase.

The compounds of formula (I) may further be convened into each other following art-known functional group transformation procedures.

A number of intermediates and starting materials in the foregoing preparations are known compounds which may be prepared according to art-known methodologies of preparing said or similar compounds. The procedures for preparing some other intermediates will be described hereinafter in more detail.

The intermediates of formula (III) can be prepared by converting the corresponding alcohols of formula (IV) with a reagent capable of converting an alcohol function into an appropriate leaving group, e.g. thionyl chloride, phosphoryl chloride, phosphorous tribromide, methanesulfonyl chloride, 4-methylbenzenesulfonyl chloride and the like.

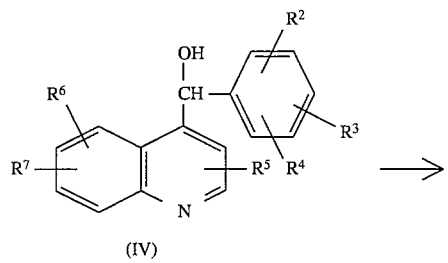

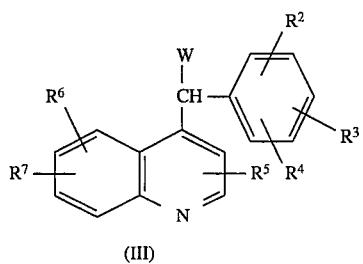

(III)

Said conversion reaction may be performed in a suitable reaction-inert solvent such as, for example, a halogenated hydrocarbon, e.g. dichloromethane, trichloromethane and the like. Optionally, an appropriate base is added, such as, for example, a tertiary amine, e.g. N,N-diethylethanamine, N,N-di(1-methylethyl)ethanamine and the like.

The alcohols of formula (IV) can be prepared by reacting an intermediate of formula (IX) with magnesium in a reaction-inert solvent such as, for example, an ether, e.g. 1,1'-oxybisethane, tetrahydrofuran and the like, optionally in the presence of a catalyst, e.g. 1,2-dibromoethane, iodine and the like and then reacting the resulting Grignard compound with a reagent of formula (X).

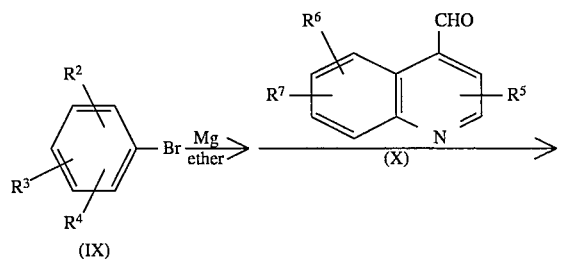

(IX)

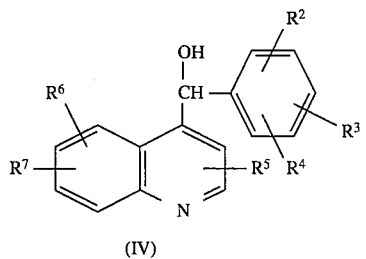

(IV)

The procedures for the synthesis of quinoline carboxaldehydes are extensively described in "Quinolines (Part III)" (G. Jones ed.), The Chemistry of Heterocyclic Compounds (Vol. 32), Wiley & Sons, Chichester (1990). In particular, the intermediates of formula (X) can be prepared by oxidation of an intermediate of formula (XI) in a reaction-inert solvent, such as, for example, an aromatic hydrocarbon, e.g. benzene, methylbenzene, chlorobenzene, bromobenzene and the like.

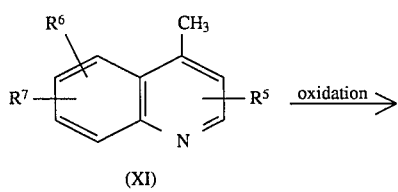

(XI)

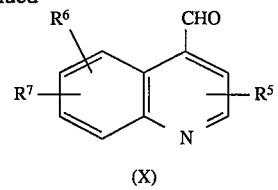

(X)

An appropriate oxidizing reagent in the above reaction is, for example, selenium dioxide, dichlorodioxochromate and the like.

Alternatively, the intermediates of formula (X) may be prepared by the reduction of the corresponding carboxylic acid of formula (XII).

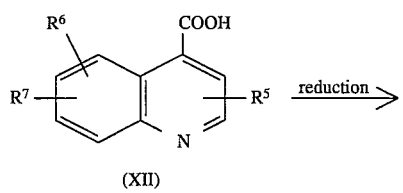

(XII)

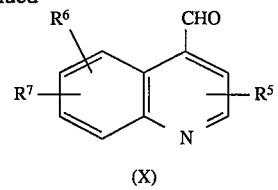

(X)

Intermediates of formula (XII) and methods of preparing them are known in the art, e.g. from "Quinolines (Pan I)" (G. Jones ed.), The Chemistry of Heterocyclic Compounds (Vol. 32), Wiley & Sons, London (1977). Said document also describes the preparation of 4-methylquinolines of formula (XI).

For example, the 4-methylquinolines of formula (XI) can be prepared by reacting an intermediate of formula (XIII) with a reagent of formula (XIV-a) or (XIV-b) in a reaction-inert solvent in the presence of an acid.

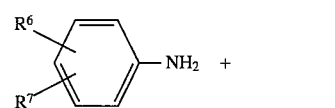

(XIII)

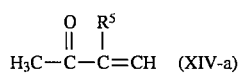

or

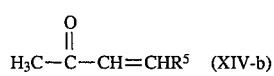

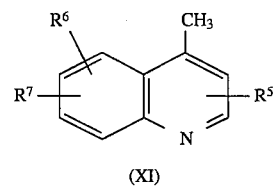

(XI)

The above reaction is preferably conducted in the presence of an acid, preferably a Lewis acid such as, for example, zinc chloride, iron (III) chloride, aluminum oxide, aluminum chloride and the like, or a mixture of these Lewis acids. A suitable reaction-inert solvent in the above reaction is for example, an alcohol, e.g. ethanol, methanol and the like.

Instead of the reagents (XIV-a) or (XIV-b) there may also be used a reagent of formula

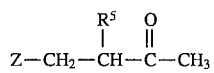 (XV-a)

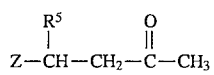 (XV-b)

or

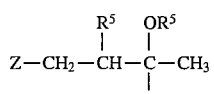 (XVI-a)

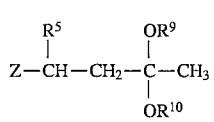 (XVI-b)

wherein

Z represents hydroxy, halo, $C_{1-4}$alkyloxy or di($C_{1-4}$alkyl)amino and $R^9$ and $R^{10}$ represent $C_{1-4}$alkyl or $R^9$ and $R^{10}$ taken together represent a $C_{2-6}$alkanediyl radical.

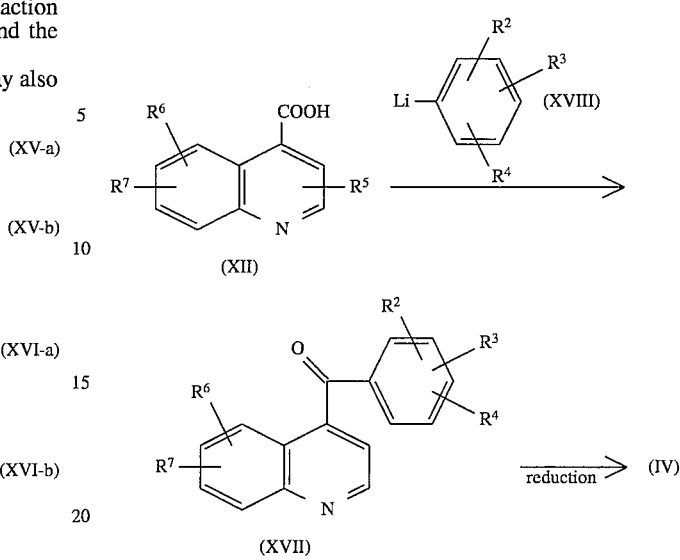

The intermediates of formula (V) and (VII) may be prepared by the following reaction sequence:

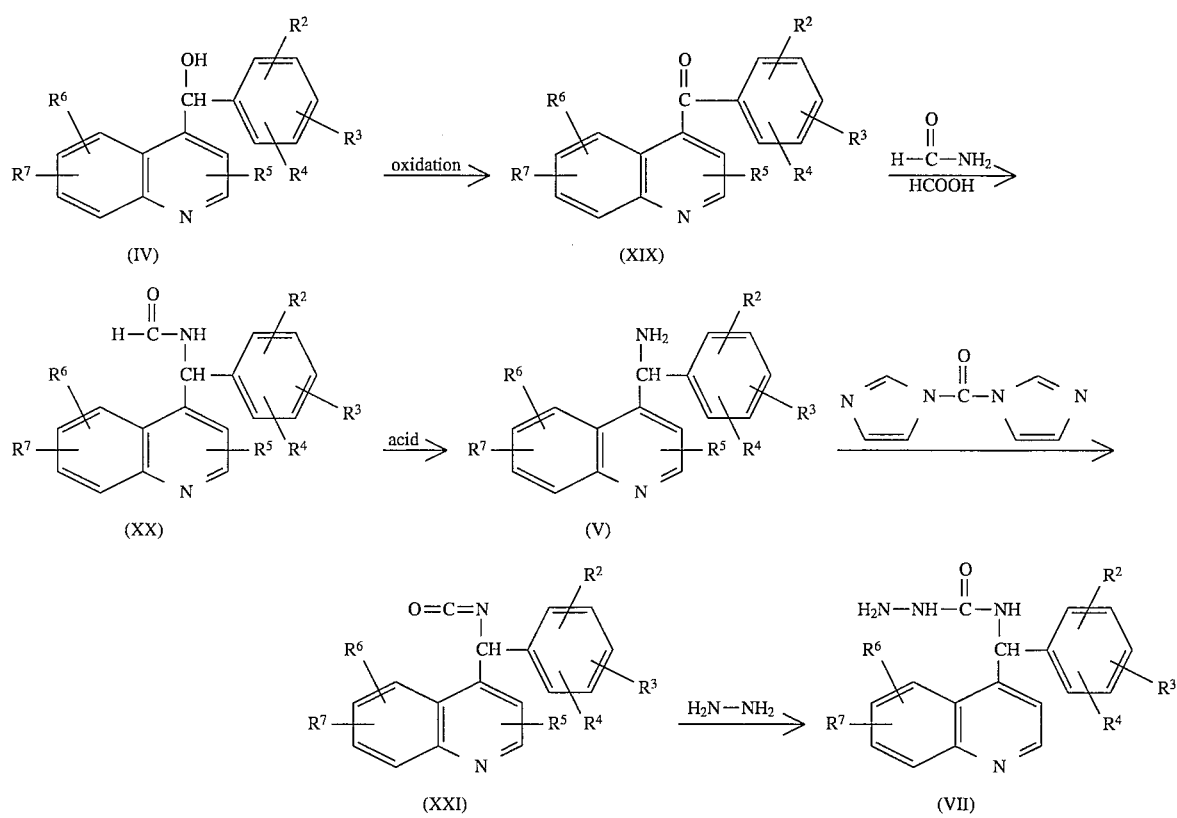

The intermediates of formula (IV) can also be prepared from the corresponding ketones of formula (XVII) following art-known reduction procedures. Said ketones are conveniently prepared by reacting a carboxylic acid of formula (XII) with a suitable phenyl lithium reagent of formula (XVIII).

The oxidation of (IV) to (XIX) may be done using a suitable oxidizing reagent, e.g. the Jones reagent or potassium permanganate, preferably in the presence of a base, e.g. tris-(2-(2-methoxyethoxy)ethyl)amine, and the like. The intermediate ketone of formula (XIX) may subsequently be transformed into the amine of formula (V), by reductive amination. When using formamide and formic acid, the intermediate amide of formula (XX) may be isolated. Intermediate (XX) is then further reacted into intermediate (V) in the presence of an acid in a suitable solvent, e.g. hydrochloric acid in 2-propanol. The reaction of (V) into (XXI) and (XXI) into (VII) is conveniently conducted in a reaction-inert solvent, e.g. tetrahydrofuran.

Further, the intermediates of formula (IV) can be converted into each other following art-known functional group transformation procedures.

For example, the intermediates of formula (IV) wherein $R^5$ is halo, $C_{1-4}$alkyloxy, amino or mono- or di($C_{1-4}$alkyl)amino can be prepared from corresponding intermediates of formula (IV) wherein $R^5$ is hydroxy. First said corresponding compounds of formula (IV) wherein $R^5$ is hydroxy are oxidized to carbonyl compounds of formula (XIX) wherein $R^5$ is hydroxy. These carbonyl compounds of formula (XIX) wherein $R^5$ is hydroxy are then treated with a suitable halogenating reagent, e.g. phosphoryl chloride, 2,4,6,-trifluorotriazine and the like, to yield intermediates of formula (XIX) wherein $R^5$ is halo. In order to prepare intermediates of formula (XIX) wherein $R^5$ is $C_{1-4}$alkyloxy, the halo derivatives described above are reacted with $C_{1-4}$alkyl-O-M, wherein M is an alkali metal cation e.g. sodium, potassium and the like, in the corresponding alkanol, e.g. sodium methoxide in methanol. In order to prepare intermediates of formula (XIX) wherein $R^5$ is amino or mono- or di($C_{1-4}$alkyl)amino, the halo derivatives are reacted with ammonia or mono- or di($C_{1-4}$alkyl)amine in a reaction-inert solvent, e.g. acetonitrile. The carbonyl compounds of formula (XIX) may then be reduced to the corresponding hydroxy intermediates of formula (IV) using a suitable reducing reagent, e.g. sodium borohydride in a reaction-inert solvent, e.g. methanol.

The compounds of formula (I), the pharmaceutically acceptable acid addition salts, the stereochemically isomeric forms thereof, the quaternized forms thereof and the N-oxides thereof, display useful pharmacological activity against Helicobacter species; e.g. *Helicobacter pylori, Helicobacter mustelae, Helicobacter felis, Helicobacter muridarum, Helicobacter nemestrinae* and the like, in particular *Helicobacter pylori*.

Particularly important in this context is the finding that the subject compounds show inhibitory activity against the growth of Helicobacter as well as in vitro bactericidal activity against said bacteria. The bactericidal effect on Helicobacter was determined with suspension cultures by means of a procedure described in Antimicrob. Agents Chemother., 1991, vol. 35, pp. 869–872.

An interesting feature of the present compounds relates to their highly specific activity against Helicobacter. The compounds of formula (I) were found to show no inhibitory activity against any of the following species: *Campylobactor jejuni, Campylobacter coli, Campylobacter fetus, Campylobacter sputorum*, Vibrio spp., *Staphylococcus aureus* and *Escherichia coli*, tested at concentrations up to $10^{-5}$M.

An important asset of the present compounds is their sustained activity against *H. pylori* at pH below the normal neutral pH. Activity at a low pH in vitro may indicate that a compound is not adversely affected by the acidic environment of the stomach in vivo.

Consequently, the subject compounds are considered to be valuable therapeutical drugs for treating warm-blooded animals, particularly humans, suffering from Helicobacter related diseases or afflictions. Examples of said diseases or afflictions are gastritis, stomach ulcers, duodenal ulcers and gastric cancer.

In view of their useful anti-Helicobacter properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

When the pharmaceutical composition takes the form of an aqueous solution, those compounds of formula (I) which display low solubility may be formulated as a salt form, or a co-solvent may be added which is water-miscible and physiologically acceptable e.g. dimethylsulfoxide and the like, or the compounds of formula (I) may be solubilized with a suitable carrier, e.g. a cyclodextrin (CD) or in particular a cyclodextrin derivative such as the cyclodextrin derivatives described in U.S. Pat. No. 3,459,731, EP-A-149, 197 (Jul.24, 1985), EP-A-197,571 (Oct. 15, 1986), U.S. Pat. No. 4,535,152 or WO 90/12035 (Oct. 18, 1990). Typically such derivatives comprise α-, β- or γ-CD wherein one or more hydroxyl groups are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl; carboxy$C_{1-6}$alkyloxy$C_{1-6}$alkyl, particularly carboxymethoxypropyl or carboxyethoxypropyl or $C_{1-6}$alkylcarbonyloxy$C_{1-6}$alkyl, particularly 2-acetyloxypropyl. Especially noteworthy as complexants and/or solubilizers are β-CD, 2,6-dimethyl-β-CD and in particular 2-hydroxypropyl-β-CD, 2-hydroxyethyl-β-CD, 2-hydroxyethyl-γ-CD, 2-hydroxypropyl-γ-CD and (2-carboxymethoxy)propyl-γ-CD. In the aforementioned cyclodextrin derivatives, the DS (degree of substitution, i.e. the average number of substituted hydroxy functions per glucose unit) is preferably in the range of 0.125 to 3, in particular 0.2 to 2, or 0.2 to 1.5. More preferably the DS ranges from about 0.2 to about 0.7, in particular from about 0.35 to about 0.5 and most particularly is about 0.4. The MS (molar degree of substitution, i.e. the average number of moles of the substituting agent per glucose unit) is in the range of 0.125 to 10, in particular of 0.3 to 3, or 0.3 to 1.5. More preferably the MS ranges from about 0.3 to about 0.8, in particular from about 0.35 to about 0.5 and most particularly is about 0.4. The most preferred cyclodextrin derivative for use in the compositions of the present invention is hydroxypropyl-β-cyclodextrin having a MS in the range of from 0.35 to 0.50 and containing less than 1.5% unsubstituted β-cyclodextrin. The amount of the cyclodextrin or ether derivative thereof in the final composition generally ranges from about 1% to about 40%, particularly from 2.5% to 25% and more particularly from 5 % to 20%.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Helicobacter related diseases said compounds may be used as medicines in Helicobacter related disorders. The compounds of the present invention also provide a method of treating warm-blooded animals, in particular humans, suffering from Helicobacter related diseases, said method comprising the systemic administration of a pharmaceutically effective amount of a compound of formula (I), a pharmaceutically acceptable addition salt thereof, a quaternized form thereof or a N-oxide thereof in admixture with a pharmaceutical carrier. In general it is contemplated that an effective daily amount would be from 0.05 mg/kg to 100 mg/kg body weight, preferably from 0.1 mg/kg to 50 mg/kg body weight and more preferably form 0.5 mg/kg to 5 mg/kg body weight. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

Optionally, other active compounds used for the eradication of Helicobacter can be administered in combination with the quinoline compounds of the present invention. The administration may occur separately (i.e. simultaneously, concurrently or consecutively) or the different drugs may be combined in one dosage form. The preferred compounds for a combination therapy are bismuth compounds, e.g. bismuth subcitrate, bismuth subsalicylate, and the like, and proton pump inhibitors, e.g. omeprazole, lansoprazole, and the like.

EXPERIMENTAL PART

A. Preparation of the Intermediates

EXAMPLE 1

A mixture of 2,3-dichlorobenzenamine monohydrochloride (0.308 mol), iron(III) chloride (0.52 mol) and zinc chloride (0.0308 mol) in ethanol (800 ml) was heated at 65° C. for 30 minutes. 3-butenone (0.308 mol) in ethanol (200 ml) was added dropwise at 65° C. over a 1 hour period and the mixture was stirred and refluxed overnight. The mixture was cooled to room temperature and evaporated. The residue was taken up in water, basified with $NH_4OH$, filtered off and extracted with ethyl acetate. The organic layer was extracted with 3N HCl. The aqueous layer was basified with $NH_4OH$ and extracted with ethyl acetate. The organic layer was dried ($MgSO_4$) and evaporated, yielding 38g (58%) of 7,8-dichloro-4-methylquinoline (interm. 1).

In a similar manner there were also prepared:
5,8-dichloro-4-methylquinoline (interm. 2); and
4-methyl-8-(trifluoromethyl)quinoline (interm. 3).

EXAMPLE 2

A mixture of intermediate (1) (0.141 mol) and selenium(IV) oxide (0.28 mol) in bromobenzene (300 ml) was stirred and refluxed for 2 hours. The mixture was filtered off and the filtrate was evaporated. The residue was taken up in cyclohexane. The precipitate was filtered off and air-dried, yielding 23 g (71%) of 7,8-dichloro-4-quinolinecarboxaldehyde (interm. 4).

In a similar manner there were also prepared:
6-bromo-4-quinolinecarboxaldehyde (interm. 5);
5,8-dichloro-4-quinolinecarboxaldehyde (interm. 6);
6-(trifluoromethyl)-4-quinolinecarboxaldehyde (interm. 7); and
8-(trifluoromethyl)-4-quinolinecarboxaldehyde (interm. 8).

EXAMPLE 3

1-bromo-3-chlorobenzene (0.15 mol) was added dropwise over a 20 minutes period to a mixture of magnesium (0.15 mol) in 1,1'-oxybisethane (100 ml). The mixture was stirred at room temperature for 30 minutes. The mixture was cooled till 0° C. and intermediate (4) (0.075 mol) in tetrahydrofuran (200 ml) was added dropwise over a 1 hour period. The mixture was poured into ice water with $NH_4Cl$ and extracted with ethyl acetate. The organic layer was dried ($MgSO_4$) and evaporated. The residue was crystallized from 1,1'-oxybisethane/ethyl acetate, yielding 18 g (70%) of (±)-7,8-dichloro-α-(3-chlorophenyl)-4-quinolinemethanol (interm. 9)

Following the same procedure, there were also prepared:

TABLE 1

| Int. No. | $R^2, R^3, R^4$ | $R^5$ | $R^6, R^7$ | melting point |
|---|---|---|---|---|
| 10 | 3-Cl | H | H | 164.0° C. |
| 11 | 4-F | H | H | 150.0° C. |
| 12 | 4-Cl | H | H | 130.8° C. |
| 13 | 2-Cl | H | H | 190.6° C. |
| 14 | 3-F | H | H | 130.4° C. |
| 15 | 3-$CF_3$ | H | H | — |
| 16 | 3,5-Cl | H | H | 210° C. |
| 17 | 3,4-Cl | H | H | 156° C. |
| 18 | 4-$OCH_3$ | H | H | 114° C. |
| 19 | 3-Cl | 2-OH | H | 250° C. |
| 20 | 3-Cl | H | 6-Cl | 190° C. |
| 21 | 3-Cl | H | 6-$OCH_3$ | 185° C. |
| 22 | 3-Cl | H | 8-Cl | 155° C. |
| 23 | 3-Cl | H | 5,8-$OCH_3$ | 180° C. |
| 24 | 3-Cl | H | 6-Br | 170° C. |
| 25 | 3-Cl | H | 8-$OCH_3$ | 188° C. |
| 26 | 3-Cl | H | 5,8-Cl | 102° C. |
| 27 | 3-Cl | H | 6-$CF_3$ | — |
| 28 | 3-Cl | H | 8-$CF_3$ | — |
| 53 | 3-Cl | 2-$CH_3$ | H | 146.2° C. |

EXAMPLE 4

Thionylchloride (17 ml) was added dropwise at 0°–5° C. to a mixture of intermediate (9) (0.05 mol) in dichloromethane (200 ml) and the mixture was stirred at room temperature overnight. The mixture was evaporated in vacuo. The residue was taken up in dichloromethane and washed with an aqueous solution of sodium hydrogen carbonate.

The organic layer was dried (MgSO$_4$) and evaporated, yielding 17.8 g (99.7%) of (±)-7,8-dichloro-4-[chloro(3-chlorophenyl)methyl]quinoline (interm. 29). Following the same procedure, there were also prepared:

TABLE 2

| Int. No. | R$^2$, R$^3$, R$^4$ | R$^5$ | R$^6$, R$^7$ | melting point |
|---|---|---|---|---|
| 30 | 3-Cl | H | H | 66.4° C. |
| 31 | 4-F | H | H | — |
| 32 | 4-Cl | H | H | — |
| 33 | H | H | H | — |
| 34 | 3-F | H | H | — |
| 35 | 3-CF$_3$ | H | H | — |
| 36 | 2-Cl | H | H | — |
| 37 | 3,5-Cl | H | H | 112.1° C. |
| 38 | 3,4-Cl | H | H | — |
| 39 | 3-Cl | 2-OH | H | — |
| 40 | 3-Cl | H | 6-Cl | — |
| 41 | 3-Cl | H | 6-OCH$_3$ | — |
| 42 | 3-Cl | H | 6,8-Cl | — |
| 43 | 3-Cl | H | 8-Cl | — |
| 44 | 3-Cl | H | 8-F | — |
| 45 | 3-Cl | H | 6-F | — |
| 46 | 3-Cl | H | 5,8-OCH$_3$ | — |
| 47 | 3-Cl | H | 6-Br | — |
| 48 | 3-Cl | H | 8-OCH$_3$ | — |
| 49 | 3-Cl | H | 5,8-Cl | — |
| 50 | 3-Cl | H | 6-CF$_3$ | — |
| 51 | 3-Cl | H | 8-CF$_3$ | — |
| 54 | 3-Cl | 2-CH$_3$ | H | — |
| 61 | 3-Cl | 2-N(CH$_3$)$_2$ | H | — |

EXAMPLE 5

Methanesulfonyl chloride (0.052 mol) was added dropwise under nitrogen atmosphere to a mixture of intermediate (18) (0.026 mol) and N,N-diethylethanamine (0.065 mol) in dichloromethane (70 ml) at 0° C. and the mixture was stirred at 0° C. for 4 hours. A saturated aqueous sodium hydrogen carbonate solution was added at 0° C. and extracted with dichloromethane. The organic layer was dried (MgSO$_4$) and evaporated. The product was used without further purification, yielding 13 g (±)-α-(4-methoxyphenyl)-4-quinolinemethanol methanesulfonate (ester) (interm. 52).

EXAMPLE 6 a) A mixture of intermediate (19) (0.118 mol) in 2-propanone (350 ml) was cooled till 0° C. The Jones reagent, chromium(VI)oxide (0.267 mol) in water (77 ml) and sulfuric acid 36N (23 ml), was added dropwise and the mixture was stirred at room temperature overnight. The mixture was basified with potassium carbonate (powder). The precipitate was filtered off and washed with water. The precipitate was extracted with a mixture of dichloromethane and acetic acid and the filtrate was evaporated. The residue was taken up in a NaHCO$_3$ solution, filtered off and washed with water. The precipitate was filtered off and air-dried, yielding 21.6 g (64%) of 4-(3-chlorobenzoyl)-2(1H)-quinolinone (interm. 55).

b) A mixture of intermediate (55) (0.07 mol) in phosphorus oxychloride (60 ml) was stirred at 60° C. for 4 hours. The mixture was evaporated and the residue was taken up in a NaHCO$_3$ solution. The precipitate was filtered off and washed with water. The precipitate was filtered off and air-dried, yielding 20 g (94%) of (3-chlorophenyl)-(2-chloro-4-quinolinyl)methanone (interm. 56).

c) A mixture of intermediate (56) (0.04 mol) in dimethylamine (150 ml) and acetonitrile (100 ml) was stirred at 50° C. for 24 hours. The mixture was evaporated in vacuo. The residue was taken up in water and extracted with a mixture was dichloromethane/ethyl acetate. The organic layer was extracted with HCl 3N. The aqueous layer was basified with NaOH and extracted with a mixture of dichloromethane and ethyl acetate. The organic layer was dried (MgSO$_4$) and evaporated, yielding 10.5 g (84%) of (3-chlorophenyl)[2-(dimethylamino)-4-quinolinyl]methanone (interm. 57).

d) Sodium borohydride (0.036 mol) was added portionwise to a solution of intermediate (57) (0.032 mol) in methanol (100 ml) at 0° C. and the mixture was stirred at room temperature for 12 hours. The mixture was poured into ice water and filtered off. The precipitate was washed with water and air-dried. The product was used without further purification, yielding 9.27 g (92%) of (±)-α-(3-chlorophenyl)-2-(dimethylamino)- 4-quinolinemethanol (interm. 58).

In a similar way there were prepared:

(±)-α-(3-chlorophenyl)-2-methoxy-4-quinolinemethanol (interm. 59); and (±)-α-(3-chlorophenyl)-2-fluoro-4-quinolinemethanol (interm. 60).

EXAMPLE 7

Sodium methoxide (0.152 mol) was added to a solution of intermediate (56) (0.033 mol) in methanol (100 ml) at room temperature and the mixture was stirred and refluxed for 24 hours. The mixture was evaporated in vacuo and the residue was taken up in ethyl acetate. The organic layer was dried (MgSO$_4$), filtered off and evaporated. The residue was purified by column chromatography over silica gel (eluent: cyclohexane/CH$_2$Cl$_2$ 50/50) (35–75 μm). The pure fractions were collected and evaporated, yielding 6.8 g (69%) of (3-chlorophenyl)(2-methoxy-4-quinolinyl)methanone (interm. 62).

EXAMPLE 8

Intermediate (55) (0.0423 mol) and 2,4,6-trifluoro-1,3,5-triazine (0.0634 mol) were heated in an autoclave at 175° C. for 2 hours. The mixture was evaporated, the residue was taken up in ethyl acetate, filtered off and the filtrate was washed with NaOH 3N. The product was extracted with ethyl acetate. The organic layer was dried (MgSO$_4$), filtered off and evaporated. The residue was purified by column chromatography over silica gel (eluent: CH$_2$Cl$_2$). The pure fractions were collected and evaporated. The product was recrystallized from 1,1'-oxybisethane, yielding 1.4 g (12%) of (3-chlorophenyl)(2-fluoro-4-quinolinyl)methanone; mp. 93.2° C. (interm. 63).

EXAMPLE 9 a) A mixture of intermediate (10) (0.02595 mol), tris(2-(2-methoxyethoxy)ethyl)amine (0.0009 mol) and potassium permanganate (0.02076 mol) in dichloromethane (200 ml) was stirred at room temperature for 12 hours. The mixture was filtered through celite and the solvent was evaporated in vacuo. The precipitate was recrystallized from 2,2'-oxybispropane/cyclohexane, yielding 6 g (87%) of (3-chlorophenyl)(4-quinolinyl)methanone; mp. 92.7° C. (interm. 64).

b) A mixture of intermediate (64) (0.029 mol) and formamide (0.15 mol) in formic acid (16 ml) was heated at 130° C. for 24 hours. The mixture was cooled to room temperature, poured into water and extracted with ethyl acetate. The ethyl acetate layer was extracted with HCl 3N. The aqueous layer was basified with NH$_4$OH and extracted with ethyl acetate. The organic layer was dried (MgSO$_4$) and evaporated. The residue was purified by column chromatography over silica gel (eluent: CH$_2$Cl$_2$/CH$_3$OH 98/2) (70–200 μm). The pure fractions were collected and evaporated. The residue (6 g) was crystallized from ethyl acetate/ 2,2'-oxybispropane, yielding 2.7 g (30%) of (±)-N-[(3-chlorophenyl)-4-quinolinylmethyl]formamide; mp. 136.3° C. (interm. 65).

c) A mixture of intermediate (65) (0.0707 mol) in hydrochloric acid 6N (250 ml) and 2-propanol (400 ml) was stirred and refluxed overnight. The mixture was cooled to room temperature, poured into ice water, basified with NH$_4$OH and extracted with ethyl acetate. The organic layer was washed with water, dried (MgSO$_4$) and evaporated. The residue was converted into the ethanedioic acid salt (2:3) and recrystallized from 2-propanone, yielding 2.5 g of (±)-α-(3-chlorophenyl)-4-quinolinemethanamine ethanedioate(2:3).hemihydrate; mp. 196.1° C. (interm. 66).

d) 1,1'-Carbonylbis-1H-imidazole (0.257 mol) in tetrahydrofuran was added to a solution of the base of intermediate (66) (0.0857 mol) in tetrahydrofuran at room temperature and the mixture was stirred for 1 hour. The product was used without further purification, yielding 25 g (99%) of (±)-4-[(3-chlorophenyl)isocyanatomethyl]quinoline (interm. 67).

e) Hydrazine (0.428 mol) in tetrahydrofuran was added to a solution of intermediate (67) (0.0856 mol) in tetrahydrofuran at room temperature and the mixture was stirred for 1 hour. The mixture was evaporated in vacuo. The residue was taken up in dichloromethane and washed with saturated aqueous NaCl. The organic layer was dried (MgSO$_4$), filtered off and evaporated. The residue was purified by column chromatography over silica gel (eluent: CH$_2$Cl$_2$/CH$_3$OH/NH$_4$OH 96/4/0.2). The pure fractions were collected and evaporated. The residue was recrystallized from dichloromethane/methanol/ethyl acetate, yielding 1.3 g (4.6%) of (±)-N-[(3-chlorophenyl)-4-quinolinylmethyl]hydrazinecarboxamide; mp. 187.1° C. (interm. 68).

B. Preparation of the Final Compounds

EXAMPLE 10

A mixture of intermediate (30) (0.0427 mol), 1,2,4-triazole (0.217 mol) and potassium carbonate (0.214 mol) in acetonitrile (200 ml) was stirred and refluxed for 12 hours. The solvent was evaporated. The crude residue was stirred in water and this mixture was extracted with dichloromethane. The separated organic layer was dried (MgSO$_4$), filtered and the solvent was evaporated. The residue (15 g) was purified by column chromatography over silica gel (300 g; 70–200 μm; eluent: CH$_2$Cl$_2$/CH$_3$OH 98/2). Two desired fractions were collected.

The first fraction was evaporated. The residue (4.8 g) was converted into the ethanedioic acid salt (1:1) and the salt was recrystallized from a mixture of methanol, 2-propanone and 1,1'-oxybisethane. The crystals were filtered off and dried, yielding 3.1 g (17.7 %) of 4-[(3-chlorophenyl)(1H-1,2,4-triazol-1-yl)methyl]quinoline ethanedioate (1:1), mp. 165.8° C. (comp. 1).

The second desired column fraction was evaporated and the residue was crystallized from 2-propanone and 2,2'-oxybispropane. The crystals were filtered off and dried, yielding 0.9 g (6.6%) 4-[(3-chlorophenyl)(4H-1,2,4-triazol-4-yl)methyl]quinoline; mp. 203.3° C. (comp. 2).

EXAMPLE 11

A mixture of intermediate (34) (0.018 mol), 1H-imidazole (0.092 mol) and potassium carbonate (0.05 mol) in 1,1'-oxybis[2-methoxyethane] (80 ml) was stirred and refluxed for 4 hours. The mixture was cooled to room temperature, poured into water and extracted with ethyl acetate. The organic layer was separated, dried (MgSO$_4$) and evaporated. The residue was purified by column chromatography over silica gel (eluent: CH$_2$Cl$_2$ and then CH$_2$Cl$_2$/CH$_3$OH 98/2) (35–70 μm). The pure fractions were collected and evaporated. The residue (7.5 g) was crystallized from 2-butanone, yielding 1.2 g (21%) of (±)-4-[(3-fluorophenyl)(1H-imidazol-1-yl)methyl]quinoline, mp. 140.3° C. (comp. 48).

EXAMPLE 12

A mixture of intermediate (33) (0.033 mol) and 1H-imidazole (0.16 mol) in 1,1'-oxybis[2-methoxyethane] (130 ml) was refluxed for 4 hours. The mixture was cooled to room temperature, poured into water and extracted with ethyl acetate. The organic layer was dried (MgSO$_4$) and evaporated. The residue was purified by column chromatography over silica gel (eluent: CH$_2$Cl$_2$/CH$_3$OH 98/2) (35–70 μm). The pure fractions were collected and evaporated. The residue (7.2 g) was crystallized from 2-butanone, yielding 2.9 g (30%) of (±)-4-[(1H-imidazol-1-yl)-phenylmethyl]quinoline; mp. 143.0° C. (comp. 59).

EXAMPLE 13

A dispersion of sodium hydride 80% (0.1 mol) was added portionwise to N,N-dimethylformamide. 1H-1,2,3,4-tetrazol (0.1 mol) in N,N-dimethylformamide was added dropwise at 0° C. and the mixture was stirred at room temperature for 15 minutes. Intermediate 30 (0.034 mol) in N,N-dimethylformamide was added dropwise at room temperature and the mixture was heated at 100° C. for 8 hours. The mixture was poured into ice water and extracted with ethyl acetate. The organic layer was extracted with 3N HCl. The acidic aqueous layer was basified with NH$_4$OH and extracted with ethyl acetate. The organic layer was dried (MgSO$_4$) and evaporated. The residue was purified by column chromatography over silica gel (eluent: CH$_2$Cl$_2$/2-propanol 98/2) (35–70 μm). The pure fractions were collected and evaporated. Fraction 1 (2.2 g) was crystallized from 2-propanone and (C$_2$H$_5$)$_2$O, yielding 2.26 g of (±)-4-[(3-chlorophenyl)(2H-tetrazol-2-yl)methyl]quinoline ethanedioate (1:1) (20%); mp. 181.8° C. (comp. 65).

Fraction 2 (4.3 g) was crystallized from (C$_2$H$_5$)$_2$O yielding 3.47 g (±)-4-[(3-chlorophenyl)(1H-tetrazol-1-yl)methyl]quinoline (31%); mp. 131.5° C. (comp. 66).

EXAMPLE 14

A mixture of intermediate (30) (0.02 mol), 1H-pyrazole (0.1 mol) and potassium carbonate (0.06 mol) in N,N-dimethylformamide (60 ml) was heated at 80° C. for 2 days. The mixture was cooled to room temperature, poured into water and extracted with EtOAc. The organic layer was dried (MgSO$_4$) and evaporated. The residue was purified by column chromatography over silica gel (eluent: CH$_2$Cl$_2$/2-propanol 98/2) (35–70 µm). The pure fractions were collected and evaporated. The residue (2.3 g) was converted into the ethanedioic acid salt (1:1) and crystallized from 2-propanone, yielding 1.4 g (21%) of (±)-4-[(3-chlorophenyl)-1H-pyrazol-1-ylmethyl]quinoline ethanedioate (1:1); mp. 168.0° C. (comp. 67).

EXAMPLE 15

2,5-dimethoxytetrahydrofuran (0.0214 mol) was added dropwise at room temperature to a solution of intermediate (66) (0.0186 mol) in acetic acid (50 ml) and the mixture was refluxed for 10 minutes. The mixture was evaporated, the residue was taken up in ethyl acetate and washed with a K$_2$CO$_3$ solution. The organic layer was dried (MgSO$_4$), filtered off and evaporated till dryness. The residue was purified by column chromatography over silica gel (eluent: CH$_2$Cl$_2$/CH$_3$OH 98.5/1.5) (15–40 µm). The pure fractions were collected and evaporated. The product was converted into the ethanedioic acid salt (1:1) and crystallized from 2-propanone, yielding 2.5 g (33%) of (±)-4-[(3-chlorophenyl)-1H-pyrrol-1-ylmethyl]quinoline ethanedioate(1:1); mp. 177.4° C. (comp. 79).

EXAMPLE 16

Diethyl azodicarboxylate (0.0174 mol) in tetrahydrofuran (15 ml) was added at 0° C. to a solution of intermediate (60) (0.0169 mol), 1,2,4-triazole (0.0174 mol) and triphenylphosphine (0.0174 mol) in tetrahydrofuran (70 ml) and the mixture was stirred at room temperature for 4 hours. The mixture was evaporated in vacuo, the residue was taken up in ethyl acetate and washed with a K$_2$CO$_3$ solution. The organic layer was dried (MgSO$_4$), filtered off and evaporated till dryness. The residue was purified by column chromatography over silica gel (eluent: CH$_2$Cl$_2$/CH$_3$OH 98/2) (15–40 µm): The pure fractions were collected and evaporated. The residue (1.9 g) was crystallized from 1,1'-oxybisethane, yielding 1.35 g (23%) of (±)-4-[(3-chlorophenyl)-1H-1,2,4-triazol-1-ylmethyl]-2-fluoroquinoline; mp. 139.8° C. (comp. 80).

EXAMPLE 17

Methanimidamide acetate (0.0918 mol) was added to a solution of intermediate (68) (0.0306 mol) in ethanol (100 ml) at room temperature and the mixture was refluxed for 3 hours. The mixture was evaporated in vacuo. The residue was taken up in dichloromethane and washed with saturated aqueous NaCl. The organic layer was dried (MgSO$_4$), filtered off and evaporated. The residue was purified by column chromatography over silica gel (eluent: CH$_2$Cl$_2$/CH$_3$OH/NH$_4$OH 97/3/0.1 ). The pure fractions were collected and evaporated. The residue was recrystallized from 2-propanone/1,1'-oxybisethane, yielding 1.25 g (16%) of (±)-4-[(3-chlorophenyl)-4-quinolinylmethyl]-2,4-dihydro-3H-1,2,4-triazol-3-one; mp. 244.3° C. (comp. 82).

EXAMPLE 18

A mixture of compound (49) (0.00625 mol) and iodomethane (0.01375 mol) in 2-propanone (30 ml) was stirred at room temperature overnight. The precipitate was filtered off, washed with 2-propanone and air-dried, yielding 2.2 g of (±)-1-[(3-chlorophenyl )-4-quinolinylmethyl]-3-methyl-1H-imidazolium iodide (76.4%); mp. 231.3° C. (comp. 68).

EXAMPLE 19

Compound (1) (0.0012 mol) was liberated in water with NH$_4$OH. The product was extracted with dichloromethane. The organic layer was dried, filtered off and evaporated. The residue was purified on Chiracell OD (eluent: hexane/C$_2$H$_5$OH 60/40). The suitable fractions were collected and evaporated.

Fraction 1 was purified again on a glass filter over silica gel (eluent: CH$_2$Cl$_2$/CH$_3$OH 95/5). The pure fractions were collected and evaporated, yielding 0.16 g of (+)-4-[(3-chlorophenyl)(1H-1,2,4-triazol-1-yl)methyl]quinoline; [a]$_D$=100.35° (c=0.114 in methanol) (comp. 70).

Fraction 2 was purified again on a glass filter over silica gel (eluent: CH$_2$Cl$_2$/CH$_3$OH 95/5). The pure fractions were collected and evaporated, yielding 0.073 g (−)-4-[(3-chlorophenyl)(1H-1,2,4-triazol-1-yl)methyl]quinoline (comp. 69).

EXAMPLE 20

3-Chlorobenzeneperoxoic acid (0.06254 mol) was added portionwise over a 10 minutes period to a mixture of compound (49) (0.03127 mol) in dichloromethane (200 ml) and the mixture was stirred at room temperature for 4 hours. A solution of saturated aqueous NaHCO$_3$ was added and the mixture and extracted with dichloromethane. The organic layer was dried (MgSO$_4$) and evaporated. The residue was purified by column chromatography over silica gel (eluent: CH$_2$Cl$_2$/CH$_3$OH 96/4). The pure fractions were collected and evaporated. The residue was crystallized from 2-butanone and 1,1'-oxybisethane, yielding 1.4 g (64 %) of (±)-4-[(3-chlorophenyl)(1H-imidazol-1-yl)methyl]quinoline, 1-oxide; mp. 184.1° C. (comp. 83).

All compounds listed in Tables 3 and 4 were prepared following methods of preparation described in examples 10–20, as is indicated in the column Ex. No.

TABLE 3

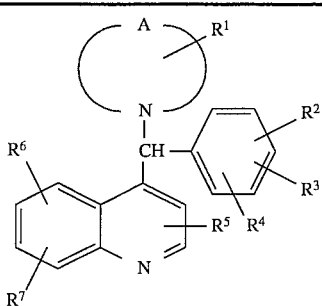

| Co. no. | Ex. No. | A—R¹ | R², R³, R⁴ | R⁵ | R⁶, R⁷ | Physical data |
|---|---|---|---|---|---|---|
| 1 | 10 | —N=CH—N=CH— | 3-Cl | H | H | mp. 165.8° C./*(1:1) |
| 2 | 10 | —CH=N—N=CH— | 3-Cl | H | H | mp. 203.3° C. |
| 3 | 10 | —N=CH—N=CH— | 4-F | H | H | mp. 85.6° C./½H₂O |
| 4 | 10 | —CH=N—N=CH— | 4-Cl | H | H | mp. 195.2° C./*(2:3) |
| 5 | 10 | —CH=N—N=CH— | H | H | H | mp. 207.6° C./*(1:1) |
| 6 | 10 | —N=CH—N=CH— | H | H | H | mp. 135.9° C./½H₂O |
| 7 | 10 | —N=CH—N=CH— | 3-F | H | H | mp. 162.7° C./*(1:1) |
| 8 | 10 | —CH=N—N=CH— | 3-F | H | H | mp. 189.5° C. |
| 9 | 10 | —N=CH—N=CH— | 3-CF₃ | H | H | mp. 120.5° C. |
| 10 | 10 | —N=CH—N=CH— | 2-Cl | H | H | mp. 142.9° C. |
| 11 | 10 | —N=CH—N=CH— | 4-Cl | H | H | mp. 127.2° C. |
| 12 | 10 | —N=CH—N=CH— | 3,5-Cl | H | H | mp. 135.6° C. |
| 13 | 10 | —N=CH—N=CH— | 3,4-Cl | H | H | mp. 135.8° C. |
| 14 | 10 | —N=CH—N=CH— | 4-OCH₃ | H | H | mp. 134.1° C. |
| 15 | 10 | —CH=N—N=CH— | 3-Cl | H | 6-Cl | mp. 163.9° C./H₂O |
| 16 | 10 | —N=CH—N=CH— | 3-Cl | H | 6-Cl | mp. 153.9° C. |
| 17 | 10 | —N=CH—N=CH— | 3-Cl | H | 6-OCH₃ | mp. 132.0° C. |
| 18 | 10 | —N=CH—N=CH— | 3-Cl | H | 6,8-Cl | mp. 217.4° C. |
| 19 | 10 | —N=CH—N=CH— | 3-Cl | H | 8-Cl | mp. 131.5° C. |
| 20 | 10 | —N=CH—N=CH— | 3-Cl | H | 7,8-Cl | mp. 175.7° C. |
| 21 | 10 | —CH=N—N=CH— | 3-Cl | H | 7,8-Cl | mp. 240.7° C. |
| 22 | 10 | —CH=N—N=CH— | 3-Cl | H | 6,8-Cl | mp. 211.1° C./H₂O |
| 23 | 10 | —N=CH—N=CH— | 3-Cl | H | 8-F | mp. 113.1° C. |
| 24 | 10 | —CH=N—N=CH— | 3-Cl | H | 6-F | mp. 228.5° C. |
| 25 | 10 | —CH=N—N=CH— | 3-Cl | H | 5,8-OCH₃ | mp. 179.9° C. |
| 26 | 10 | —CH=N—N=CH— | 3-Cl | H | 8-F | mp. 170.5° C./½H₂O |
| 27 | 10 | —CH=N—N=CH— | 3-Cl | H | 6-Br | mp. 131.3° C./H₂O |
| 28 | 10 | —N=CH—N=CH— | 3-Cl | H | 6-Br | mp. 161.0° C. |
| 29 | 10 | —CH=CH—N=N— | 3-Cl | H | H | mp. 145.9° C. |
| 30 | 10 | —CH=N—CH=CH— | 3-Cl | H | 8-OCH₃ | mp. 174.4° C. |
| 31 | 10 | —N=CH—N=CH— | 3-Cl | H | 5,8-OCH₃ | mp. 189.6° C. |
| 32 | 10 | —N=CH—N=CH— | 3-Cl | H | 5,8-Cl | mp. 187.2° C. |
| 33 | 10 | —CH=N—N=CH— | 3-Cl | H | 5,8-Cl | mp. 211.4° C. |
| 34 | 10 | —N=CH—N=CH— | 3-Cl | H | 8-OCH₃ | mp. 174.8° C. |
| 35 | 10 | —N=CH—N=CH— | 3-Cl | 2-OH | H | mp. 249.4° C. |
| 36 | 10 | —N=CH—N=CH— | 3-Cl | H | 6-F | mp. 95.4° C./½H₂O |
| 37 | 10 | —CH=N—CH=CH— | 3-Cl | H | 8-F | mp. 154.5° C. |
| 38 | 10 | —CH=N—CH=CH— | 3-Cl | H | 6-CF₃ | mp. 115.1° C./½H₂O |
| 39 | 10 | —CH=N—CH=CH— | 3-Cl | H | 8-CF₃ | mp. 161.9° C. |
| 40 | 10 | —N=C(NH₂)—N=CH— | 3-Cl | H | H | mp. 232.7° C. |
| 41 | 10 | —N=CH—N=C(NH₂)— | 3-Cl | H | H | mp. 251.8° C. |
| 42 | 10 | —CH=N—CH=CH— | 3-Cl | H | 6-Br | mp. 208.7° C./*(2:3)/½H₂O |
| 43 | 10 | —CH=N—CH=CH— | 3-Cl | H | 6,8-Cl | mp. 198.7° C. |
| 44 | 10 | —CH=N—CH=CH— | 3-Cl | H | 5,8-Cl | mp. 168.1° C. |
| 45 | 10 | —N=CH—CH=N— | 3-Cl | H | H | mp. 128.1° C. |
| 46 | 10 | —CH=N—CH=CH— | 3-Cl | H | 6-F | mp. 144.5° C. |
| 47 | 10 | —N=CH—N=CH— | 3-Cl | H | H | mp. 103.4°/½H₂O |
| 48 | 11 | —CH=N—CH=CH— | 3-Cl | H | H | mp. 140.3° C. |
| 49 | 11 | —CH=N—CH=CH— | 3-Cl | H | H | mp. 121.0° C. |
| 50 | 11 | —CH=N—C(NO₂)=CH— | 3-Cl | H | H | mp. 194.5° C. |
| 51 | 11 | —CH=N—CH=CH— | 3-Cl | 2-OH | H | mp. >260° C. |
| 52 | 11 | —CH=N—CH=CH— | 4-OCH₃ | H | H | mp. 111.6° C. |
| 53 | 11 | —CH=N—CH=CH— | 3-CF₃ | H | H | mp. 172.5 ° C. |
| 54 | 11 | —CH=N—C(CH₃)₄ CH— | 3-Cl | H | H | mp. 182.7° C./*(2:3) |
| 55 | 11 | —CH=N—CH=CH— | 3-Cl | H | 6-Cl | mp. 134.4° C. |
| 56 | 11 | —CH=N—CH=CH— | 3-Cl | H | 6-OCH₃ | mp. 177.3° C./*(2:3) |
| 57 | 11 | —CH=N—CH=CH— | 3-Cl | H | 7,8-Cl | mp. 202.9° C. |
| 58 | 11 | —CH=N—CH=CH— | 3-Cl | H | 5,8-OCH₃ | mp. 106.7° C./*(1:2)/H₂O |
| 59 | 12 | —CH=N—CH=CH— | H | H | H | mp. 143.0 C. |
| 60 | 12 | —CH=N—CH=CH— | 2-Cl | H | H | mp. 122.9° C. |

TABLE 3-continued

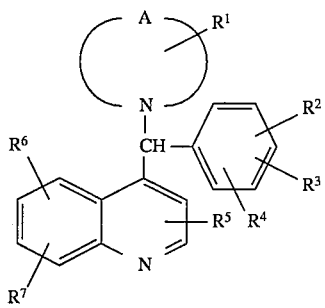

| Co. no. | Ex. No. | A—R¹ | R², R³, R⁴ | R⁵ | R⁶, R⁷ | Physical data |
|---|---|---|---|---|---|---|
| 61 | 12 | —CH=N—CH=CH— | 4-F | H | H | mp. 139.2° C. |
| 62 | 12 | —C(CH₃)=N—CH=CH— | 3-Cl | H | H | mp. 160.2° C. |
| 63 | 12 | —CH=N—CH=CH— | 3,5-Cl | H | H | mp. 194.9° C. |
| 64 | 12 | —CH=N—CH=CH— | 4-Cl | H | H | mp. 88.2° C./½H₂O |
| 65 | 13 | —N=N—CH=N— | 3-Cl | H | H | mp. 1181.8° C./*(1:1) |
| 66 | 13 | —N=N—N=CH— | 3-Cl | H | H | mp. 131.5° C. |
| 67 | 14 | —N=CH—CH=CH— | 3-Cl | H | H | mp. 168.0° C./*(1:1) |
| 68 | 18 | —CH=N⁺(CH₃)—CH=CH— | 3-Cl | H | H | mp. 231.3° C./.I⁻ |
| 69 | 19 | —N=CH—N=CH— | 3-Cl | H | H | —/(−) |
| 70 | 19 | —N=CH—N=CH— | 3-Cl | H | H | $[\alpha]_D = +100.35°$ (c = 0.114 in methanol) |
| 71 | 19 | —CH=N—CH=CH— | 3-Cl | H | H | mp. 136.3° C./(+)/ $[\alpha]_D = +102.32°$ (c = 0.496 in methanol) |
| 72 | 19 | —CH=N—CH=CH— | 3-Cl | H | H | mp. 141.4° C./(−) $[\alpha]_D = -103.29$ (c = 0.492 in methanol) |
| 74 | 10 | —CH=CH—N=CH— | 3-Cl | 2-N(CH₃)₂ | H | mp. 155.5° C. |
| 75 | 10 | —CH=CH—N=CH— | 3-Cl | H | 8-Cl | mp. 161.5° C./.HNO₃ |
| 76 | 10 | —N=CH—N=CH— | 3-Cl | H | 6-CF₃ | mp. 110.9° C. .HNO₃.H₂O |
| 77 | 10 | —CH=CH—N=CH— | 3-Cl | 2-CH₃ | H | mp. 157.8° C. |
| 78 | 10 | —N=CH—N=CH— | 3-Cl | 2-CH₃ | H | mp. 205.8° C./* |
| 79 | 15 | —CH=CH—CH=CH— | 3-Cl | H | H | mp. 177.4° C./* |
| 80 | 16 | —N=CH—N=CH— | 3-Cl | 2-F | H | mp. 139.8° C. |
| 81 | 16 | —N=CH—N=CH— | 3-Cl | 2-OCH₃ | H | mp. 191.4° C. |
| 82 | 17 | —CH=N—NH—C(=O)— | 3-Cl | H | H | mp. 244.3° C. |

*= ethanedioate

TABLE 4

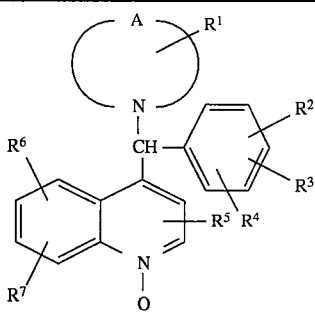

| Co. No. | Ex. No. | A—R¹ | R², R³, R⁴ | R⁵ | R⁶, R⁷ | Physical data |
|---|---|---|---|---|---|---|
| 83 | 20 | —CH=CH—N=CH— | 3-Cl | H | H | mp. 184.1° C. |
| 84 | 20 | —N=CH—N=CH— | 3-Cl | H | H | mp. 150.8° C. |

C. Pharmacological Example

The anti-Helicobacter activity of the subject compounds was assessed by the following in-vitro test procedure.

Activity of test compounds versus Helicobacter

The activity of test compounds against *Helicobacter pylori* was determined against a standard set of 5 *H. pylori* strains obtained from clinical material. Minimal inhibitory concentrations (MICs) were determined by measuring the activity of *H. pylori* urease after treatment of growing cultures of the bacteria with the antimicrobial agents.

The test compounds were dissolved in DMSO at a concentration of $10^{-3}$M. A dilution to $10^{-4}$M in DMSO was also prepared. 10 µl volumes of these solutions were pipetted in the wells of Repli-Dishes (®Sterilin). Wells containing DMSO alone were included as controls in each Repli-Dish. Ampicillin ((+)-6-[(2-amino-2phenylacetyl)amino]-3,3-dimethyl-7-oxo-4-thia-1-azabicyclo[3.2.0]heptane-2-carboxylic acid.trihydrate) and metronidazole (2-methyl-5-nitro-1H-imidazol-lethanol) were included as reference compounds in each batch of tests. (These compounds were tested at final concentrations of $10^{-5}$, $10^{-6}$, $10^{-7}$ and $10^{-8}$M). Test plates were stored at 4° C. until used.

The five isolates of *H. pylori* were maintained by subculture on 10% blood agar every 2 or 3 days. The bacteria were grown at 37° C. under a microaerophilic atmosphere containing 5% oxygen, 10% $CO_2$ and 85% nitrogen. Suspensions of *Helicobacter pylori* for inoculum were prepared in Brain-heart infusion broth and adjusted to an absorbance of 1.5±0.3 at 530 nM.

Freshly prepared 10% blood agar held at 45° C. was added in 1 ml volumes to the wells of the test plates, thus diluting the test compounds to $10^{-5}$ and $10^{-6}$M. The medium was allowed to cool, then 10 µl volumes of bacterial suspension were pipetted on the agar surface. The plates were incubated for 48 h at 37° C. under the microaerophilic atmosphere described above. To facilitate reading of the plates and to ensure that any growth on the media was truly *H. pylori*, advantage was taken of the highly potent urease activity unique to this species. After the 48 h of incubation, 1 ml volumes of urease broth were gently added to each Repli-Dish well and the plates were incubated at 37° C. for 2 h. 100 µl samples of fluid from each well were then pipetted into the wells of 96-place microdilution plates. A purple colour was interpreted as growth, yellow-orange as no growth of *H. pylori*. By this means a clear end-point was obtained, from which the inhibitory effects could be determined. All compounds that showed activity at either of the two concentrations tested was retested with further dilutions included to establish the MIC and with a broader spectrum of bacterial species as target organisms.

Table 5 summarizes the MIC values (µM) determined against 5 *H. pylori* strains for a set of compounds of the present invention.

TABLE 5

| | *H. pylori* strains | | | | |
|---|---|---|---|---|---|
| Co. No. | 11916 | 6553 | 6548 | 6544 | 4326 |
| 1 | 1 | 1 | 1 | 1 | 1 |
| 3 | 10 | 10 | 10 | 10 | 10 |
| 6 | 10 | 10 | 10 | 10 | 10 |
| 7 | 1 | 1 | 1 | 1 | 1 |
| 8 | 10 | 10 | 10 | 10 | >10 |
| 10 | ND | 1 | 1 | 10 | 10 |
| 19 | 10 | 10 | 10 | 10 | 10 |
| 23 | 1 | 1 | 1 | 1 | 1 |
| 29 | 1 | 1 | 1 | 1 | 1 |
| 36 | 1 | 1 | 1 | 10 | 1 |
| 37 | 1 | 1 | 1 | 1 | 1 |
| 40 | 10 | 10 | 10 | 10 | 10 |
| 41 | 10 | 10 | 10 | 10 | 10 |
| 45 | 10 | 10 | 10 | 10 | 10 |
| 46 | 10 | 10 | 10 | 10 | 10 |
| 48 | 1 | 1 | 0.1 | 0.1 | 1 |
| 49 | 1 | 0.1 | 0.1 | 0.1 | 1 |
| 55 | 10 | 10 | 10 | 10 | 10 |
| 59 | 1 | 1 | 0.1 | 0.1 | 1 |
| 60 | 10 | 10 | 10 | 10 | 10 |
| 61 | 10 | 10 | 10 | 10 | 10 |

TABLE 5-continued

| | *H. pylori* strains | | | | |
|---|---|---|---|---|---|
| Co. No. | 11916 | 6553 | 6548 | 6544 | 4326 |
| 62 | 10 | 10 | 10 | 10 | >10 |
| 65 | 1 | 1 | 1 | 1 | 1 |
| 66 | 1 | 1 | 1 | 1 | 10 |
| 67 | 1 | 1 | 1 | 1 | 1 |
| 68 | 10 | 10 | 10 | ND | 10 |
| 69 | 0.1 | 0.1 | 0.1 | 0.1 | 0.1 |
| 71 | 1 | 1 | 1 | ND | 1 |
| 72 | 0.1 | 0.1 | 0.1 | ND | 0.1 |
| 74 | >10 | >10 | >10 | 10 | >10 |
| 75 | 1 | 1 | 10 | 1 | 1 |
| 77 | 10 | 10 | 10 | 10 | 10 |
| 78 | 10 | 10 | 10 | 10 | 10 |
| 79 | 1 | 1 | 1 | 1 | 1 |
| 80 | 10 | 10 | 10 | 10 | 10 |
| 84 | 1 | 1 | 10 | 1 | 1 |

ND: Not determined

D. Compositions Examples

"Active ingredient" (A.I.) as used throughout these examples relates to a compound of formula (I), a pharmaceutically acceptable acid addition salt or a stereochemically isomeric form thereof.

EXAMPLE 21

Oral Drops

500 Grams of the A.I. was dissolved in 0.5 l of 2-hydroxypropanoic acid and 1.5 l of the polyethylene glycol at 60°≈80° C. After cooling to 30°≈40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 22

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 23

Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10,000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 24

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

EXAMPLE 25

Suppositories

3 Grams A.I. was dissolved in a solution of 3 grams 2,3-dihydroxybutanedioic acid in 25 ml polyethylene glycol 400. 12 Grams surfactant and triglycerides q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

EXAMPLE 26

Cyclodextrin Containing Formulation 100 ml of propylene glycol is treated with 3.76 ml concentrated HCl, stirred and slightly heated. 10 g A.I. is added and stirring is continued until homogeneous. In a separate vessel, 400 g hydroxypropyl-β-cyclodextrin is dissolved in 400 ml distilled water. The solution of the active ingredient is added slowly to the cyclodextrin solution while stirring. The sorbitol solution (190 ml) is added and stirred till homogeneous. The sodium saccharin (0.6 g) is dissolved in 50 ml distilled water and added to the mixture. The flavours are added and the pH of the mixture (about 1.7) is adjusted with a 10N NaOH solution to pH 2.0±0.1. The resulting solution is diluted with distilled water to an end volume of 1 liter. A pharmaceutical dosage form is obtained by filtering the previous solution and filling it into suitable containers. e.g. in 100 ml glass bottles with a screw cap.

We claim:

1. A compound having the formula

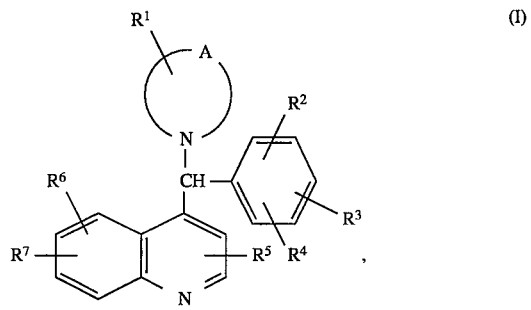

a pharmaceutically acceptable acid addition salt thereof, a stereochemically isomeric form thereof, a pharmaceutically acceptable quaternized form thereof or an N-oxide thereof, wherein —A— represents a bivalent radical of formula

| —N=CH—CH=CH— | (a), |
| —CH=N—CH=CH— | (b), |
| —N=N—CH=CH— | (c), |
| —N=CH—N=CH— | (d), |
| —N=CH—CH=N— | (e), |
| —CH=N—N=CH— | (f), |
| —N=N—N=CH— | (g), |
| —N=N—CH=N— | (h), | or

| —CH=CH—CH=CH— | (i); |

$R^1$, $R^2$, $R^3$, $R^4$, $R^5$, $R^6$ and $R^7$ each independently represent hydrogen, halo, hydroxy, $C_{1-4}$alkyloxy, $C_{1-4}$alkyl, trifluoromethyl, amino, mono- or di($C_{1-4}$alkyl)amino or nitro, provided that when one substituent on an aromatic ring is a nitro then the other substituents on said aromatic ring are other than nitro.

2. A compound according to claim 1 wherein $R^1$ represents hydrogen, $C_{1-4}$alkyl, hydroxy, $C_{1-4}$alkyloxy, nitro, amino or mono- or di($C_{1-4}$alkyl)amino; $R^2$, $R^3$ and $R^4$ each independently represent hydrogen, halo, trifluoromethyl, hydroxy or $C_{1-4}$alkyloxy;

$R^5$ represents hydrogen, halo, hydroxy or $C_{1-4}$alkyloxy;

$R^6$ and $R^7$ each independently represent hydrogen, halo, hydroxy, $C_{1-4}$alkyloxy or trifluoromethyl.

3. A compound according to claim 2 wherein $R^1$, $R^2$, $R^3$, $R^5$ and $R^6$ represent hydrogen, and $R^4$ and $R^7$ each independently represent hydrogen or halo.

4. A compound according to claim 3 wherein —A— represents a bivalent radical of formula

| —N=N—CH=CH— | (c) | or

| —N=CH—N=CH— | (d) | and $R^4$ is 3-halo.

5. A compound according to claim 4 which is selected from the group consisting of 4-[(3-chlorophenyl)(1 H-1,2,4-triazol-1-yl)methyl]quinoline, the pharmaceutically acceptable acid addition salts thereof, the stereochemically isomeric forms thereof, the pharmaceutically acceptable quaternized forms thereof and the N-oxides thereof.

6. A pharmaceutical composition comprising as an active ingredient a therapeutically effective amount of a compound as defined in claim 1 and a pharmaceutically effective carrier.

7. A pharmaceutical composition comprising as an active ingredient a therapeutically effective amount of a compound as defined in claim 2 and a pharmaceutically effective carrier.

8. A pharmaceutical composition comprising as an active ingredient a therapeutically effective amount of a compound as defined in claim 3 and a pharmaceutically effective carrier.

9. A pharmaceutical composition comprising as an active ingredient a therapeutically effective amount of a compound as defined in claim 4 and a pharmaceutically effective carrier.

10. A pharmaceutical composition comprising as an active ingredient a therapeutically effective amount of a compound as defined in claim 5 and a pharmaceutically effective carrier.

11. A method of treating patients suffering from Helicobacter infection which comprises administering to such patients a therapeutically effective amount of a compound as defined in claim 1.

12. A method of treating patients suffering from Helicobacter infection which comprises administering to such patients a therapeutically effective amount of a compound as defined in claim 2.

13. A method of treating patients suffering from Helicobacter infection which comprises administering to such patients a therapeutically effective amount of a compound as defined in claim 3.

14. A method of treating patients suffering from Helicobacter infection which comprises administering to such patients a therapeutically effective amount of a compound as defined in claim 4.

15. A method of treating patients suffering from Helicobacter infection which comprises administering to such patients a therapeutically effective amount of a compound as defined in claim 5.

* * * * *